United States Patent [19]

Usukura

[11] 4,326,509
[45] Apr. 27, 1982

[54] THERMOPLASTIC COMPOSITION FOR SETTING BANDAGES AND A SOLVENTLESS PROCESS FOR THE MANUFACTURE THEREOF

[75] Inventor: Koji Usukura, Saitama, Japan

[73] Assignee: Tokyo Eizai Laboratory Co. Ltd., Tokyo, Japan

[21] Appl. No.: 105,200

[22] Filed: Dec. 19, 1979

[30] Foreign Application Priority Data

Dec. 27, 1978 [JP] Japan .................................. 53/161383

[51] Int. Cl.³ .......................... A61F 5/04; B05D 3/02; B32B 7/01
[52] U.S. Cl. ..................................... 128/90; 427/374.1; 427/389.8; 427/392; 427/389.9; 427/430.1; 427/439; 525/176; 525/177; 525/444; 428/264; 428/265; 428/268
[58] Field of Search ......................... 128/155, 156, 90; 427/374.1, 389.8, 389.9, 392, 430.1, 439; 525/170, 176, 177, 444; 428/481, 482, 483, 264, 265, 268

[56] References Cited

U.S. PATENT DOCUMENTS

| Re. 30,102 | 9/1979 | Thomas et al. ................. 428/482 X |
| 3,426,754 | 2/1969 | Bierenbaum et al. ............... 128/156 |
| 4,046,837 | 9/1977 | Carroll ............................... 525/177 |
| 4,204,987 | 5/1980 | Streets ........................... 428/481 X |
| 4,206,844 | 6/1980 | Thakamoto et al. ........... 428/481 X |
| 4,214,040 | 7/1980 | Meyer et al. ................... 428/482 X |
| 4,217,426 | 8/1980 | McConnell et al. ............ 525/177 X |

FOREIGN PATENT DOCUMENTS 525886 6/1956 Canada ............................ 427/374.1

*Primary Examiner*—Michael R. Lusignan
*Attorney, Agent, or Firm*—Kenyon & Kenyon

[57] ABSTRACT

The invention herein relates to a thermoplastic suitable for setting bandages and a solventless process for the manufacture of setting bandages therewith. The thermoplastic composition comprises a saturated linear polyester and a resin with low crystallizability and a low softening temperature. The setting bandage made according to this invention can be easily applied to injured parts of a body and the cast resulting therefrom is light, inert, waterproof, ventilative, rigid and shockproof. A method for the manufacture of said setting bandages without the use of solvents is also described in detail.

12 Claims, 1 Drawing Figure

Apparatus For Manufacture Of Thermoplastic Setting Bandage

Apparatus For Manufacture Of Thermoplastic Settling Bandage

… … …

THERMOPLASTIC COMPOSITION FOR SETTING BANDAGES AND A SOLVENTLESS PROCESS FOR THE MANUFACTURE THEREOF

INTRODUCTION

The invention relates to a new thermoplastic resin composition for setting bandages for orthopedic treatment and a method for the manufacture of the setting bandages therewith. A thermoplastic resin composition is provided which is sufficiently plastic within a relatively low temperature range of 55° to 80° C. such that the setting bandage prepared therewith can readily and quickly be applied to any portion of the human body but would not stick to the hands of the operator, and, after solidification, the case is ventilative, waterproof, not contaminative, inert, highly rigid and shock-proof. The thermoplastic resin can be prepared in an environmentally safe manner without the use of solvents. A method for the manufacture of setting bandages with such a thermoplastic resin has also been developed.

BRIEF DESCRIPTION OF THE FIGURE

The FIGURE is a perspective view of an apparatus for the manufacture of a setting bandage according to this invention. The numbers in the drawing indicate the following: (1) the base fabric, (2) tension device, (3) vessel for fluid resin, (4) heater, (5) oil, (6) rolls for adjusting thickness, (7) hot air blast, (8) cooling rolls and (9) take up rolls.

BACKGROUND OF THE INVENTION

Figure 1:
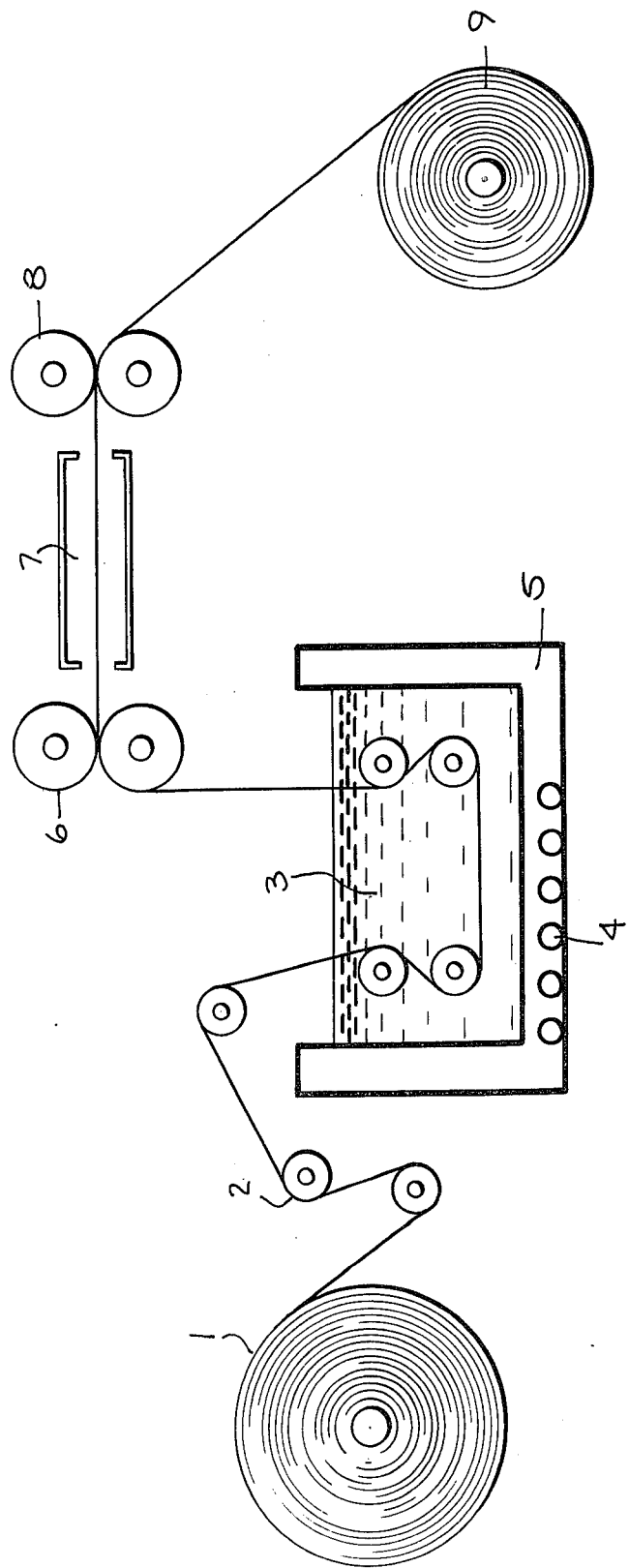

The conventional setting bandage is a gypsum bandage, wherein calcined gypsum (plaster of Paris) is impregnated into a fabric. However, there are many drawbacks to the use of the gypsum bandage. The resulting cast is very heavy. The drying time is very long since a large amount of water is required to cause gypsum to solidify. The cast is difficult to modify after it sets. It loses its strength when exposed to moisture, such as rain, snow or water. As a result, the cast often has to be rewound. A gypsum cast lacks sufficient ventilativity and tends to cause the growth of molds and bacteria. Also, it lacks sufficient transparency to x-rays thereby making x-ray diagnosis difficult. In addition, during manufacture, the pulverized particles of calcined gypsum affect the workmen and may cause them to contract bronchitis. Accordingly, various setting bandages avoiding the use of calcined gypsum have been proposed. For example, Japanese Pat. No. 6116/73, entitled "Bandage for orthopedic surgery, impregnated with ultra-violet-ray hardenable plastic", Japanese Pat. No. 152586/75, entitled, "Surgery bandage impregnated with photo-hardenable resin", and Japanese Pat. No. 146786/76, entitled "Photo-hardenable splint for orthopedic surgery", are hard and light fastening bandages, wherein a bandage of woven, knitted or non-woven fabric having been impregnated with a photo-sensitive resin is adapted to wind or to splint the wounded portion up to a necessary thickness, and then solidified by exposing it to an ultra-violet ray lamp (usually, at about 3,000 Å).

By virtue of the above-mentioned invention, setting bandages have been greatly improved. A setting bandage which is highly plastic and applicable to any and all parts of the body is available. The resulting cast is very rigid, light and waterproof with improved ventilability and x-ray penetrability. However, because of the high reactivity and the low molecular weight of the polymers employed as the main component of the composition, patients can develop skin irritation and the odor may cause dizziness. Gloves are also necessary for the operator and a dark room is required to handle the photo-sensitive resin. Thus, mass production of the bandage is very difficult.

Other setting bandages known in the art are described in the following:

Japanese Pat. No. 95435/73 entitled "Thermo-contractive moldings", Japanese Pat. No. 25086/75 entitled "Thermo-plastic material for bandage or modeling", Japanese Pat. No. 147190/75 entitled "A material for plastic surgery", Japanese Pat. No. 95896/77 entitled "Thermo-plastic body supporter", Japanese Pat. No. 6797/78 entitled "Moldable gypsum material", and Japanese Pat. No. 64192/77 entitled "Bandage material and stiff-supporting bandage", wherein, generally, a thermo-plastic resin is coated on or impregnated into a woven or knitted, relatively coarse textured, base fabric prepared from cotton, glass wool or synthetic fiber or mixtures of the above to form into a coiled or sheet bandage, or said thermoplastic resin itself is formed into a plate to be applied to any object.

These prior art patents describe the use of relatively high molecular weight polymers to decrease the effects of bad odors. However, these polymers are low in plasticity, are less adhesive, and require high temperatures for softening. They are also less stable. The bandages made therefrom do not produce a good fit. These disadvantages result in a decrease in their use in spite of the improvements. In carrying out the above invention, it was found that no particular room is necessary for working and mass production is possible. However, the high softening temperature and high viscosity of the resins require the use of organic solvents, e.g., toluene, trichloroethylene, trichloromethylene, methylethylketone, tetrahydrofuran, for the coating or impregnation of these resins. Thus, dangers of fire or pollution of the environment can be expected.

BRIEF DESCRIPTION OF THE INVENTION

Attempts have been made to remove these disadvantages. An excellent resin composition has been prepared. These compositions are sufficiently plastic within a low temperature range. The softened resins do not tend to adhere to the human body, but the bandages prepared therefrom can be easily and quickly applied to the body. After the resin has hardened, the cast has high mechanical strength and high rigidity, is highly durable, waterproof, shockproof and inert. Without the use of solvents, the resin composition can also be coated on or impregnated into fine or coarse textured woven or knitted fabrics consisting of the following or a mixture of the following, cotton, glass wool or synthetic fibers.

DETAILED DESCRIPTION OF THE INVENTION

According to the present invention, a resin composition for setting bandages is provided consisting of a saturated linear polyester which is a relatively low crystallizable resin with a relatively low softening temperature. This composition can be coated on or impregnated into thick soft fabrics with large openings without the use of solvents.

The embodiments of the invention are described in detail in the following examples which are presented for purposes of illustration and are not meant to limit or define the invention. The words "parts" or "%" relate to weight units unless otherwise stated.

Table I shows seven examples of resin compositions, the blending ratios and physical characteristics thereof, e.g., softening temperature, adhesives, waterproofness, strength, viscosity and decomposition temperature.

Polyhexa-methylene-adipate is not commercially available. It can be prepared by combining 1,6-hexanediol and adipic acid. A mixture of 1.05 moles of 1,6-hexanediol and 1 mole of adipic acid is heated in a stream of nitrogen gas. When the temperature exceeds the melting point of 1,6-hexanediol, the mixture is agitated. After the rapid dehydrating reaction has completed, an amount, corresponding to 3% of the total weight of the above, of a reaction accelerator, such as calcium acetate, sulfuric acid, potassium carbonate, 4-methyl-benzene sulfonic acid, dibutyltin dilaurate, tetraisopropyl titanate ((iso-PrO)$_4$Ti), etc. is added to the mixture, which is then heated to 190° C. The reaction is allowed to take place in a stream of nitrogen until the acid value is 5.0 and the molecular weight is about 10,000 to 13,000 resulting in a white, highly viscose product, polyhexamethyleneadipate. A small amount of titanium oxide or the like is added for the purpose of adjusting the color.

Table II shows the properties of the commercially available compositions, Bylon,RA-200 and RV-300 as indicated in Table I.

Table III shows method for measuring the characteristics of the various compositions listed in Table I. Namely, plasticity is evaluated by measuring the softening temperature and the differential caloric content; adhesivity is measured by the feeling test, waterproofness is measured by the change in compression strength after soaking in aqueous acidic, alkaline and neutral media respectively; rigidity is evaluated by measuring bending, compression and impression strength; shockproofness is estimated by the drop test; coatability without solvent is appraised by measuring the viscosity and temperature at which oxidative decomposition occurs. Test samples consist of both planar and cylindrical configurations. The blended compositions were used in tests for coatability.

Planar samples can be prepared by melting and mixing the blended composition in a heater kneader at 100°-200° C. to a homogeneous mixture. The molten resin is poured into a 3 mm thick metallic mold, cooled, and cut into rectangular pieces, 35 mm × 150 mm.

Alternately, the homogeneous mixture can be poured into a heating vessel and heated to 110° C. A base fabric knitted from cotton and glass wool is impregnated with a predetermined amount of the fluid (680 g/m$^2$) in the heated vessel through a heated roller, treated with a blast of hot air and then cooled as a sheet to produce an impregnated fabric with openings of 1 to 3 mm$^2$. A preferred thickness of the fabric used is 1 to 7 mm. The sheet is then cut into 10 cm wide bands, and rolled into a coil with a polyethylene film sandwiched between the layers. Then the coiled band is soaked in hot water at 70° C. for approximately 5 minutes to be softened. The band is subsequently wound four layers thick around a 75 mm diameter glass pipe while removing the polyethylene film. The wrapped pipe is allowed to cool. The formed cylinder is separated from the glass pipe. The temperature for oxidative decomposition and viscosity was measured at the same time as for the planar test sample. Conditions and results are indicated in Table III.

The method for preparing a bandage incorporating the above-described resin is as follows. The resin composition is heated in vessel 3 (FIG. 1) to 110° C. until it is a fluid with a viscosity of about 250,000 to 350,000 pois. A basic fabric, which may be a soft material with wide openings knitted from a comparatively low density bulky fiber, is drawn out from coil 1 into vessel 3. A predetermined amount in weight per unit area of fluid resin is impregnated onto the base fabric. Any excess is removed. The impregnated fabric is heat treated and then cooled and then wound around drum 9. The product is then cut into sheets of a certain set width and length by using a slitter machine. The sheets are then rolled into coils with a heat resistive film, such as, polyethylene, polypropylene, nylon, polyester or polyvinylchloride films, sandwiched between the layers and finished as a rolled setting bandage.

The thermoplastic bandage prepared in the above-described manner can be applied onto the body in the following manner. The coiled bandage is soaked in hot water for 3 to 5 minutes to be heated to about 70° C., softening the impregnated resin and rendering it to be sufficiently self-adhesive. The bandage is taken out of the hot water and any excess water is removed. The bandage is applied to the injured portion of the body on which a material such as cotton bandage, sponge, nonwoven cloth or felt has been applied as a cushion. The bandage is wound 3 to 4 layers thick. Meanwhile, the edges and angles can be adjusted. After this, the wound bandage is cooled, naturally, or by force, to allow it to solidify into a strong, rigid and shockproof setting cast. As can be observed from the above description as well as the illustrative examples, the bandage is softenable at relatively low temperatures (55°-80° C.) and will adhere to itself. Therefore, it can readily fit any portion of the body; and, because of its manipulatability at low temperatures and the possibility of putting additional layers on previously wound bandage when necessary, it can meet a wide range of demands. Further, because the resin does not stick to the operator's hand nor to the injured portion of the body, the operation can be performed quickly and cleanly. The set bandage is durable, waterproof, rigid and highly shockproof and can be relied on for a long period of use. In addition, because of its high strength on setting, a relatively small amount of bandage is required, it is thus more economical. It is also light and ventilative, therefore, the patient is more comfortable while wearing the cast.

It should also be emphasized that the thermoplastic resin of the setting bandage according to this invention is very stable at high temperatures and if heated to a high temperature will not undergo significant oxidation, evaporation or decomposition. Thus, the viscosity can be lowered by raising the temperature to facilitate the coating of the base fabric without the need of using a solvent.

TABLE I

| No. | Composition | Parts mixing | Softening Temperature | Adhesiveness | Water-proof | Strength | | Viscosity and Decomposition temperature |
|---|---|---|---|---|---|---|---|---|
| 1 | Polyhexa methylene adipate | 100 | 55° C.–61° C. | Not adhesive | no | A. | Bending | 19.7 × 10$^4$ |

TABLE I-continued

| No. | Composition | Parts mixing | Softening Temperature | Adhesiveness | Water-proof | | Strength | Viscosity and Decomposition temperature |
|---|---|---|---|---|---|---|---|---|
| | Bylon RA-200 | 50 | | to finger | change | | 3.3 Kg | cps/120° C. |
| | Titanium Oxide | 5 | | | | B. | Compression 16.8 Kg | 250° C. |
| | Coloring agent | 0.3 | | | | C. | Impulsive, no breakage | |
| 2 | Polyhexa methylene adipate | 100 | 55° C.–63° C. | Not adhesive to finger | no change | A. | 2.3 Kg | 23 × 10⁴ cps/120° C. |
| | Bylon RV-300 | 50 | | | | B. | 17.5 kg | 250° C. |
| | Titanium Oxide | 5 | | | | C. | No breakage | |
| | Coloring Agent | 0.3 | | | | | | |
| 3 | Polyhexa methylene adipate | 100 | 51° C.–58° C. | Not adhesive to finger, Inferior in self-adhesion | no change | A. | 1.4 Kg | 18.3 × 10⁴ cps/120° C. |
| | IBMA (Isobutil Methacrylate) | 50 | | | | B. | 12.4 Kg | 230° C. |
| | Titanium Oxide | 5 | | | | C. | No breakage | |
| | Coloring Agent | 0.3 | | | | | | |
| 4 | Polyhexa methylene adipate | 100 | 55° C.–57° C. | Slightly adhesive to finger | no change | A. | 3.0 Kg | 25.8 × 10⁴ cps/120° C. |
| | Caprolacton | 50 | | | | B. | 15.3 Kg | 220° C. |
| | Titanium Oxide | 5 | | | | C. | No breakage | |
| | Coloring agent | 0.3 | | | | | | |
| 5 | Polyhexa methylene adipate | 100 | 50° C.–55° C. | Slightly adhesive to finger | no change | A. | 1.2 Kg | 18.5 × 10⁴ cps/120° C. |
| | Polyvinylether | 30 | | | | B. | 9.4 Kg | 180° C. |
| | Titanium oxide | 5 | | | | C. | deformed | |
| | Coloring agent | 0.3 | | | | | | |
| 6 | Polyhexa methylene adipate | 100 | 55° C.–75° C. | No Adhesiveness | no change | A. | | 32 × 10⁴ cps/120° C. |
| | EVA (Ethylene vinyl acetate) | 50 | | | | B. | | 250° C. |
| | Titanium oxide | 5 | | | | | | |
| | Coloring agent | 0.3 | | | | C. | damaged | |
| 7 | Polyhexa methylene adipate | 100 | 55° C.–83° C. | No Adhesiveness | no change | A. | 1.8 Kg | 38 × 10⁴ cps/120° C. |
| | PE | 50 | | | | B. | 8.3 KG | 250° C. |
| | Titanium oxide | 5 | | | | C. | deformed | |
| | Coloring agent | 0.3 | | | | | | |

TABLE II

| Property | Bylon, RA-200 | Bylon, RV-300 | Note |
|---|---|---|---|
| Form | ⅜" dice | thin plate | |
| Color | Colorless or light yellow | Colorless or light blue | |
| Smell | no smell | no smell | |
| Solubility parameter (SP) | about 9.2 | about 8.9 | |
| Humidity % | 0.4 | 0.5 | 25° C., 60RH |
| Tensile St. Kg/cm² | 500 | 50 | D638-61T |
| Maximum elongation % | 3 | 700 | D638-61T |
| Hardness (Shore D) | 80 | 25 | 25° C. |
| Specific gravity | 1.255 | 1.192 | 25° C. |
| Index of refraction | 1.55 | 1.54 | |
| Limit viscosity | 0.53 | 0.70 | 30° C. Phenol/ tetrachloroethane |
| Molecular weight | 15,000–20,000 | 20,000–25,000 | |
| Acid value | 1.68 | 1.08 | = 6/4, 0.5% (assumption) |
| Glass Transition Temp. °C. | 67 | 6 | |
| Softening point °C. | 163 | 123 | JIS-K-2531 (Annular sphere Pr.) |
| Softening point °C. | 135 | 90 | JIS-K-2425 (Mercury process) |
| Melting temp. | 180–200 | 140–160 | |
| Melt. Viscosity, poise | 2900 | 3900 | Phot-chem.flow-tester, 200° C. 30 l/sec |
| Decrease of weight through heating % | 0.4 | 0.5 | 200° C. × 5 hr in air (moisture) |
| tan | 0.3 | 9.5 | 25° C. |

TABLE II-continued

| Property | Bylon, RA-200 | Bylon, RV-300 | Note |
|---|---|---|---|
| tan | 9.0 | 0.5 | 70° C. |
| Specific inductivity | 3.8 | 5.2 | 25° C. (D150-59T) |
| Specific inductivity | 5.0 | 6.0 | 70° C. (D150-59T) |
| Solid spc. resistance .cm | $7.2 \times 10^{16}$ | $1.3 \times 10^{15}$ | |
| Puncture voltage v/mil | 6500 | 2200 | at 1 mil |
| Ultra violet ray absorption | Shut off ultra violet ray shorter than 300 Å | | |
| Vapour permeability | 40g/24hr/m²/mil/atm | | ASTM-E96 |
| Oxygen permeability | 0.3–0.4g/24hr/m²/mil/atm | | ASTMD-1434-63 |

TABLE III

| Item testing | Process | Conditions and Equipment |
|---|---|---|
| Plasticity | Softening temperature | Test piece is kept horizontally between two supporting points, at the middle point of which 20 g of weight is applied, and temperature is measured at the point where 20 mm of variation is seen. |
| | DTA | About 1.5 mg of test piece contained in an Al-cell is measured by a differential thermal analyzer. |
| Adhesiveness | feeling test | Test piece having been heart-softened by hot water or 80° C. is pushed by finger, and taking the finger away, adhesiveness is appraised. |
| Waterproof | Compression test | A cylindrical test piece is soaked, respectively, within solutions 1N—HCl, 1N—NaCl and in water from water work for 72 hours, and taken out to be washed by water, then removing water therefrom, and compression test was performed. |
| Rigidness | Bending strength test | Horizontally keeping a plate test piece between two supporting points, with a weight added at the middle point, max. load and deformation are measured. |
| | Compression test | By means of stro-glass tester, load of deformation of 6.3 cm in a cylinder test piece is measured. |
| Resistance against Impulse | Drop test | A steel plate (10 × 10 cm) of 2 Kg is dropped from 30 cm height on a cylinder test piece, and tested whether it cracked or not. |
| Coating characteristic | temperature of oxidizing decomposition | Tested by means of DTA. |
| | Viscosity | Having the test piece heated to 120° C., it is tested by rotary viscosity meter. |

What is claimed is:

1. An orthopedic setting bandage which comprises a thick, soft, woven or knit base fabric of natural or synthetic fibers impregnated with a thermoplastic composition comprising 60% to 80% by weight of a saturated linear polyester and 20% and 40% by weight of a resin having a low crystallinity and a low softening temperature which is selected from the group consisting of polyvinyl either, a copolymer of ethylene and vinylacetate, polyisoprene, polyisobutylmethacrylate, polyethylene, poly (4-hydroxyhexanoic acid) and poly (ethylene terephthalate-ethylene heptadiate) wherein, said composition impregnated base fabric will harden to a waterproof, strong, rigid, nonporous, nontacky structure upon being warmed to about 45° C. and subsequently cooled.

2. A bandage according to claim 1 which further comprises the composition having a softening temperature of from about 55° C. to about 80° C.

3. A bandage according to claim 1 wherein the resin is poly (ethylene terephthalate ethylene heptadiate) of the trademark Bylon, RA-200 or Bylon, RV-300 which has the physical characteristics as shown in Table II.

4. A bandage according to claim 1 which composition comprises 100 parts by weight of the saturated linear polyester and a maximum of 70 parts by weight of the resin.

5. A bandage according to claim 2, 3, or 4 wherein the saturated linear polyester is poly (hexamethylene adipate) with a molecular weight greater than 5000.

6. A bandage according to claim 1 which further comprises a roll of the base fabric coated or impregnated with the composition and a separating sheet of plastic film sandwiched between adjacent layers of base fabric.

7. A method for preparing a setting bandage without the use of solvents, which comprises:
(a) forming a homogeneous thermoplastic composition by mixing 60% to 80% by weight of a saturated linear polyester and 20% to 40% by weight of a resin having a low crystallinity and a low softening temperature, which is selected from the group consisting of polyvinyl ether, a copolymer of ethylene and vinylacetate, polyisoprene, polyisobutylmethacrylate, polyethylene, poly (4-hydroxyhexanoic acid) and poly (ethylene terephthalate ethylene heptadiate);
(b) heating the composition in a vessel to about 110° C. until the composition is melted into a fluid with a viscosity of about 250,000 to 350,000 pois;
(c) immersing a thick base fabric with large openings into the heated composition until a predetermined amount of composition per unit area of fabric impregnates or coats the fabric;
(d) removing the fabric impregnated or coated with the composition from said vessel;
(e) removing any excess composition from the fabric;

(f) heating the fabric impregnated or coated with composition;

(g) cooling the fabric coated or impregnated with composition.

8. A method for preparing a setting bandage according to claim 7 wherein the base fabric used is a fabric knitted from one or a mixture of the fibers selected from the group consisting of cotton, glass and synthetic fibers.

9. A method for preparing a setting bandage according to claim 7, wherein the base fabric used is woven from one or a mixture of the fibers selected from the group consisting of cotton, glass and synthetic fibers.

10. A method for preparing a setting bandage according to claim 7 wherein the predetermined amount of resin impregnated onto the fabric is 680 g/m$^2$.

11. A method of preparing a setting bandage according to claim 7 wherein the size of the openings of the fabric after impregnation is 1 to 3 mm$^2$.

12. A method of preparing a setting bandage according to claim 7 wherein the thickness of the fabric used is 1 to 7 mm.

* * * * *

UNITED STATES PATENT AND TRADEMARK OFFICE
CERTIFICATE OF CORRECTION

PATENT NO. : 4 326 509
DATED : April 27, 1982
INVENTOR(S) : KOJI USUKURA

It is certified that error appears in the above-identified patent and that said Letters Patent are hereby corrected as shown below:

Column 1, line 16, change "case" to --cast--

Column 1, line 62, change "3,000 Å" to -- 3,6000 Å --

Column 3, line 28, change "Bylon, RA-200 and RV-300" to --Bylon -RA 200 and RV 300 --

Column 4, line 58, change "high" to --higher--

Column 7, line 66, change "either" to --ether--

Signed and Sealed this

Fourteenth Day of September 1982

[SEAL]

Attest:

GERALD J. MOSSINGHOFF

Attesting Officer        Commissioner of Patents and Trademarks

UNITED STATES PATENT AND TRADEMARK OFFICE
CERTIFICATE OF CORRECTION

PATENT NO. : 4 326 509
DATED : April 27, 1982
INVENTOR(S) : KOJI USUKURA

It is certified that error appears in the above-identified patent and that said Letters Patent are hereby corrected as shown below:

Column 1, line 16, change "case" to --cast--

Column 1, line 62, change "3,000 $\overset{o}{A}$" to -- 3,600 $\overset{o}{A}$ --

Column 3, line 28, change "Bylon, RA-200 and RV-300" to --Bylon -RA 200 and RV 300 --

Column 4, line 58, change "high" to --higher--

Column 7, line 66, change "either" to --ether--

This certificate supersedes Certificate of Correction issued September 14, 1982.

Signed and Sealed this

Twenty-third Day of November 1982

[SEAL]

Attest:

GERALD J. MOSSINGHOFF

Attesting Officer

Commissioner of Patents and Trademarks